(12) United States Patent
Qureshi et al.

(10) Patent No.: US 7,824,594 B2
(45) Date of Patent: Nov. 2, 2010

(54) PROCESS FOR ACTIVATING A WEB

(75) Inventors: Khalid Qureshi, Mason, OH (US); Fred Naval Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 7 days.

(21) Appl. No.: 12/273,611

(22) Filed: Nov. 19, 2008

(65) Prior Publication Data
US 2009/0127742 A1 May 21, 2009

Related U.S. Application Data

(60) Provisional application No. 61/003,620, filed on Nov. 19, 2007.

(51) Int. Cl.
*B29C 55/18* (2006.01)
(52) U.S. Cl. .................. 264/288.4; 264/290.2; 264/280
(58) Field of Classification Search ................. 264/280, 264/288.4, 290.2
See application file for complete search history.

(56) References Cited

U.S. PATENT DOCUMENTS

| | | | |
|---|---|---|---|
| 3,488,415 A * | 1/1970 | Patchell et al. ............... 264/154 |
| 3,692,618 A | 9/1972 | Dorschner et al. |
| 3,802,817 A | 4/1974 | Matsuki et al. |
| 3,848,594 A | 11/1974 | Buell |
| 3,860,003 A | 1/1975 | Buell |
| 3,911,173 A | 10/1975 | Sprague |
| 3,929,135 A | 12/1975 | Thompson |
| 4,116,892 A | 9/1978 | Schwarz |
| 4,200,963 A | 5/1980 | Kamfe et al. |
| 4,209,563 A | 6/1980 | Sisson |
| 4,223,063 A | 9/1980 | Sabree |
| 4,324,246 A | 4/1982 | Mullane et al. |
| 4,340,563 A | 7/1982 | Appel et al. |
| 4,342,314 A | 8/1982 | Radel et al. |
| 4,438,167 A | 3/1984 | Schwarz |
| 4,463,045 A | 7/1984 | Ahr et al. |
| 4,515,595 A | 5/1985 | Kievit et al. |
| 4,525,407 A | 6/1985 | Ness |
| 4,573,986 A | 3/1986 | Minetola et al. |

(Continued)

FOREIGN PATENT DOCUMENTS

| | | |
|---|---|---|
| EP | 1 559 388 A2 | 8/2005 |
| EP | 1 600 132 A1 | 11/2005 |
| WO | WO 94/14395 A1 | 7/1994 |
| WO | WO 95/16746 A1 | 6/1995 |

(Continued)

OTHER PUBLICATIONS

International Search Report, dated Nov. 19, 2009, 4 pages.

*Primary Examiner*—Joseph S Del Sole
*Assistant Examiner*—Kimberly A Stewart
(74) *Attorney, Agent, or Firm*—John G. Powell

(57) ABSTRACT

A process for simultaneously activating two or more portions of a web in different directions. The process involves feeding a web into an apparatus that includes a pair of intermeshing activation rolls having three dimensional surface features configured to simultaneously activate different portions a web in different directions. The three dimensional surface features are arranged in discrete regions on the rolls such that at least two of the regions provide different directions of activation. The rolls include one or more buffer regions positioned between the discrete regions on the roll that provide different directions of activation.

20 Claims, 9 Drawing Sheets

U.S. PATENT DOCUMENTS

| | | |
|---|---|---|
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |
| 4,673,402 A | 6/1987 | Weisman et al. |
| 4,695,278 A | 9/1987 | Lawson |
| 4,785,996 A | 11/1988 | Ziecker et al. |
| 4,795,454 A | 1/1989 | Dragoo |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,968,312 A | 11/1990 | Khan |
| 4,990,147 A | 2/1991 | Freeland |
| 5,006,394 A | 4/1991 | Baird |
| 5,037,416 A | 8/1991 | Allen et al. |
| 5,062,840 A | 11/1991 | Holt et al. |
| 5,092,861 A | 3/1992 | Nomura et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,171,236 A | 12/1992 | Dreier et al. |
| 5,202,173 A | 4/1993 | Wu et al. |
| 5,221,274 A | 6/1993 | Buell et al. |
| 5,246,433 A | 9/1993 | Hasse et al. |
| 5,254,111 A | 10/1993 | Cancio et al. |
| 5,260,345 A | 11/1993 | DesMarais et al. |
| 5,269,775 A | 12/1993 | Freeland et al. |
| 5,296,184 A | 3/1994 | Wu et al. |
| 5,306,266 A | 4/1994 | Freeland |
| 5,330,458 A | 7/1994 | Buell et al. |
| 5,342,338 A | 8/1994 | Roe |
| 5,354,597 A | 10/1994 | Capik et al. |
| 5,366,782 A | 11/1994 | Curro et al. |
| 5,387,207 A | 2/1995 | Dyer et al. |
| 5,422,172 A | 6/1995 | Wu |
| 5,439,458 A | 8/1995 | Noel et al. |
| 5,460,622 A | 10/1995 | Dragoo et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,569,234 A | 10/1996 | Buell et al. |
| 5,571,096 A | 11/1996 | Dobrin et al. |
| 5,607,760 A | 3/1997 | Roe |
| 5,609,587 A | 3/1997 | Roe |
| 5,625,222 A | 4/1997 | Yoneda et al. |
| 5,626,571 A | 5/1997 | Young et al. |
| 5,635,191 A | 6/1997 | Roe et al. |
| 5,643,588 A | 7/1997 | Roe et al. |
| 5,650,214 A | 7/1997 | Anderson et al. |
| 5,653,703 A | 8/1997 | Roe et al. |
| 5,865,823 A | 2/1999 | Curro |
| 5,897,545 A | 4/1999 | Kline et al. |
| 5,938,648 A | 8/1999 | LaVon et al. |
| 5,941,864 A | 8/1999 | Roe |
| 5,957,908 A | 9/1999 | Kline et al. |
| 5,968,025 A | 10/1999 | Roe et al. |
| 5,977,430 A | 11/1999 | Roe et al. |
| 5,993,432 A * | 11/1999 | Lodge et al. ............. 604/385.3 |
| 5,997,520 A | 12/1999 | Ahr et al. |
| 6,013,063 A | 1/2000 | Roe et al. |
| 6,120,487 A | 9/2000 | Ashton |
| 6,120,489 A | 9/2000 | Johnson et al. |
| 6,168,584 B1 | 1/2001 | Allen et al. |
| 6,169,151 B1 | 1/2001 | Waymouth et al. |
| 6,177,607 B1 | 1/2001 | Blaney et al. |
| 6,258,308 B1 | 7/2001 | Brady et al. |
| 6,368,444 B1 | 4/2002 | Jameson et al. |
| 6,436,080 B1 | 8/2002 | Carlucci et al. |
| 6,476,289 B1 | 11/2002 | Buell et al. |
| 6,506,329 B1 * | 1/2003 | Curro et al. ................. 264/283 |
| 6,518,378 B2 | 2/2003 | Waymouth et al. |
| 6,521,555 B1 | 2/2003 | Bodaghi et al. |
| 6,555,643 B1 | 4/2003 | Rieger |
| 6,559,262 B1 | 5/2003 | Waymouth et al. |
| 6,605,172 B1 * | 8/2003 | Anderson et al. ........... 156/199 |
| 6,680,265 B1 | 1/2004 | Smith et al. |
| 6,680,422 B2 | 1/2004 | Roe |
| 6,716,441 B1 | 4/2004 | Osborne et al. |
| 6,766,817 B2 | 7/2004 | Dias da Silva |
| 6,794,023 B1 | 9/2004 | Melik et al. |
| 6,811,643 B2 | 11/2004 | McAmish et al. |
| 6,821,612 B1 | 11/2004 | Melik et al. |
| 6,843,949 B2 | 1/2005 | Brady et al. |
| 6,884,494 B1 * | 4/2005 | Curro et al. ................. 428/196 |
| 6,918,404 B2 | 7/2005 | Dias da Silva |
| 6,926,704 B2 | 8/2005 | Andersson et al. |
| 6,936,039 B2 | 8/2005 | Kline et al. |
| 7,056,411 B2 | 6/2006 | Desai et al. |
| 7,066,586 B2 | 6/2006 | Dias da Silva |
| 7,169,288 B2 | 1/2007 | Drapeau |
| 7,201,822 B2 | 4/2007 | Schneider et al. |
| 7,222,654 B2 | 5/2007 | Schneider et al. |
| 7,223,818 B2 | 5/2007 | Autran et al. |
| 2002/0105110 A1 | 8/2002 | Dobrin |
| 2002/0112276 A1 | 8/2002 | Ruman et al. |
| 2003/0225382 A1 | 12/2003 | Tombult-Meyer et al. |
| 2003/0233082 A1 | 12/2003 | Kline et al. |
| 2004/0002691 A1 | 1/2004 | Popp et al. |
| 2004/0039364 A1 | 2/2004 | Karami |
| 2004/0092677 A1 | 5/2004 | Hanke et al. |
| 2004/0116028 A1 | 6/2004 | Bryner |
| 2004/0167486 A1 | 8/2004 | Busam et al. |
| 2004/0181200 A1 | 9/2004 | Desai et al. |
| 2004/0193133 A1 | 9/2004 | Desai et al. |
| 2004/0222553 A1 | 11/2004 | Desai et al. |
| 2004/0224132 A1 * | 11/2004 | Roe et al. ................... 428/175 |
| 2004/0238105 A1 | 12/2004 | Schneider et al. |
| 2005/0070866 A1 | 3/2005 | Isele et al. |
| 2005/0164586 A1 | 7/2005 | Autran et al. |
| 2005/0165173 A1 | 7/2005 | Autran et al. |
| 2005/0211368 A1 | 9/2005 | McGuire et al. |
| 2005/0214461 A1 | 9/2005 | Desai et al. |
| 2005/0215963 A1 | 9/2005 | Autran et al. |
| 2005/0215964 A1 | 9/2005 | Autran et al. |
| 2005/0230034 A1 | 10/2005 | Arora et al. |
| 2006/0014460 A1 | 1/2006 | Isele et al. |
| 2006/0155253 A1 | 7/2006 | Dziezok et al. |
| 2006/0155254 A1 | 7/2006 | Sanz et al. |
| 2007/0078427 A1 | 4/2007 | Raycheck et al. |
| 2007/0093769 A1 | 4/2007 | Kline et al. |
| 2008/0004591 A1 | 1/2008 | Desai et al. |
| 2008/0224351 A1 | 9/2008 | Curro et al. |

FOREIGN PATENT DOCUMENTS

| | | |
|---|---|---|
| WO | WO 95/24173 A2 | 9/1995 |
| WO | WO 98/14156 A | 4/1998 |
| WO | WO 00/29199 | 5/2000 |
| WO | WO 03/072338 | 9/2003 |
| WO | WO 2005/110748 | 11/2005 |
| WO | WO 2008/067463 | 6/2008 |

* cited by examiner 730   720

PROCESS FOR ACTIVATING A WEB

CROSS REFERENCE TO RELATED APPLICATIONS

This application claims the benefit of U.S. Provisional Application No. 61/003,620, filed Nov. 19, 2007.

FIELD OF THE INVENTION

The disclosure herein generally relates to a method for activating a stretchable material. More specifically, the disclosure relates to a method for simultaneously activating different areas of a stretchable material in different directions.

BACKGROUND OF THE INVENTION

Various articles, including disposable diapers, training pants, adult incontinence articles, feminine hygiene products, and the like utilize elastic or elastic-like materials to improve the conformability and/or fit of the article. However, the relatively high costs typically associated with some elastic materials may make their use in such articles undesirable. In addition, certain elastic materials may not provide suitable softness, smoothness, strength, etc. when incorporated into a wearable article. As a result, nonwoven fabrics, especially inexpensive polymer-based nonwoven fabrics, have found increasing popularity for use in disposable absorbent articles. Nonwoven fabrics are typically formed as webs, batts, mats, or sheets of fiber networks, and are sometimes referred to generally as "nonwoven webs." An obstacle to the use of nonwoven webs in elastic textile articles has been the relatively inelastic nature of nonwoven webs formed from extensible but inelastic fibers. Therefore, laminates formed by joining a low-force stretch elastic material to one or more layers of extensible nonwoven material are typically used to reduce or even eliminate at least some of these undesirable features. In these constructions, the elastic layer may provide the elastic stretch needed for fit and comfort, while the outer nonwoven layers provide the aesthetics necessary to make the laminate feel cloth-like. However, since the nonwoven is typically not elastic, it may still offer undesirable resistance to the extensibility of the low-force stretch elastic material (i.e., "lock up" the stretch properties of the elastic material).

One way to limit the amount of lock up caused by an inelastic material such as an extensible nonwoven, when it is laminated to an elastic material, is to activate the laminate. Activation, or incremental stretching as it is sometimes referred to, involves permanently stretching or elongating a web or portions of a web in one or more directions. As the web is stretched, some of the fibers, inter-fiber bonds, and/or intra-fiber bonds are believed to be broken. The breaking of the fibers and/or bonds of the nonwoven web may result in increased elasticity and/or softness in the web, at least to the degree of elongation. Known processes for activating an extensible material typically involve passing the material through one or more pairs of activation rolls. The activation rolls generally have three-dimensional surface features (e.g., teeth and grooves, peaks and channels, or corrugations), which are configured to operatively engage one another. The three-dimensional surface features on the rolls are typically complementary (i.e., fit together in an intermeshing fashion) such that the rolls are sometimes referred to as being a "matched" or "mated" pair. As the web passes through the matched pair of activation rolls, it is subjected to relatively high localized mechanical stress from the intermeshing three-dimensional surface features. Most, if not all, of the fiber/ bond breaking takes place in these areas of high localized mechanical stress. Upon successful completion of the activation process, the activated web may exhibit an increase in length in one or more dimensions depending on the direction of activation.

In one known process for activating a material, a web is first fed through a pair of matched activation rolls that have raised portions extending in the "axial direction" of the rolls (i.e., parallel to the axis of rotation of the rolls) to activate the material in a first direction. The axially extending raised portions of the rolls intermesh in a manner similar to the way the teeth of two gears typically intermesh. The rolls may be positioned such that the intermeshing teeth do not substantially contact one another in order to avoid damaging the teeth and/or roll. As the web passes through the pair of rolls, it is activated in the direction of travel of the material, sometimes referred to as the machine-direction ("MD"). In some instances, a matched pair of rolls may include surface features that resemble a line of alternating discs of larger and smaller diameters, sometimes referred to as a ring-rolling configuration. Ring-rolling is typically used to activate a web in the direction orthogonal to the machine direction, also referred to as the cross-direction ("CD"). In some instances, the nonactivated web may be bonded to an unstrained elastic material to form a laminate material. The laminate may subsequently be subjected to an activation process to form a "zero-strain" stretch laminate. Examples of methods of activating webs and/or methods of making elastic laminates that include activated materials may be found in U.S. Pat. No. 4,200,963 to Kamfe, et al.; U.S. Pat. No. 4,209,563 to Sisson; U.S. Pat. No. 4,525,407 to Ness; U.S. Pat. No. 4,834,741 to Sabee; U.S. Pat. No. 5,143,679 to Buell, et al.; U.S. Pat. No. 5,650,214 to Anderson et al., U.S. Pat. No. 5,156,793 to Buell, et al.; U.S. Pat. No. 5,330,458 to Buell, et al.; U.S. Pat. No. 6,476,289 to Buell, et al.; U.S. Pat. No. 6,521,555 to Bodaghi, et al.; PCT Publication Nos. WO00/029199 to Jameson, et al.; WO03/072338 to McAmish, et al.; WO05/110748 to McCormack et al.; and WO08/067463 to Middlesworth, et al.; and U.S. Publication No. 20080224351 to Curro et al. While known processes may be suitable for activating a material in one direction, it may be desirable in certain applications to activate a material in more than one direction.

Another method for providing some elasticity to a substantially inelastic, extensible material is sometimes referred to as "SELFing," which means Structural Elastic-Like Film. SELFing is similar to activation in that the material is stretched between intermeshing teeth. However, in SELFing, the teeth do not run continuously along the length of the activation area and instead are discrete along the length, leaving narrow bands of nonactivated material. In the activated areas, the material deforms permanently, while in the unactivated areas, there is substantially no permanent deformation. When a SELFed material is stretched, the material typically exhibits elastic properties.

One known method for activating a web in two directions is to pass the web through a first pair of rolls that activate the web in a first direction, and then subsequently pass the web through a second (or more) pairs of rolls to activate the web in a second (or more) direction. A problem with adding additional pairs of rolls is that it may increase the cost and complexity of a manufacturing operation. In addition, adding more pairs of rolls generally means more space is required on the manufacturing line to accommodate the additional rolls. Additionally, if the different areas of the web that are to have different directions of activation are relatively close to one another (e.g., less than 20 mm apart) it is possible that due to process tracking variability, a small portion of the web may get activated twice, once in each of two directions. This double activation may put excessive strain on the web locally, resulting in pin holes, or in extreme cases, even tears in the laminate. Thus, in at least some manufacturing processes, the additional cost, complexity and/or space requirements may make the use of additional pairs of activation rolls undesirable.

Another known method for activating a web in two directions is to pass the web through a stamping operation that uses a pair of matched plates to activate portions of a web placed between the plates. The plates may include three-dimensional surface features and are typically arranged as a complementary pair of plates with an upper plate and a lower plate. One of the plates, typically the upper plate, is moved by a piston or other means toward the other plate until the three-dimensional surface features of the plates intermesh to provide the desired depth of engagement and corresponding level of activation. The three-dimensional surface features of the plates may be configured to provide activation in multiple directions and/or to different portions of a web. However, stamping operations tend to be slower than operations that employ a roll due to the reciprocating nature of a press. In addition, the precise control required for a proper depth of engagement and strain rate may slow the process even further and/or require expensive equipment and/or complex processes. In at least some commercial industries, especially those industries where a high output of products may be required for the industry to be commercially successful (e.g., the disposable diaper industry), a stamping operation may not be a commercially desirable or even commercially viable option for activating a web at high speeds.

Accordingly, it would be desirable to provide a method for activating different regions of a web in different directions with a single pair of rolls without causing undesirable damage to the web.

DETAILED DESCRIPTION

Definitions

Figure 1:
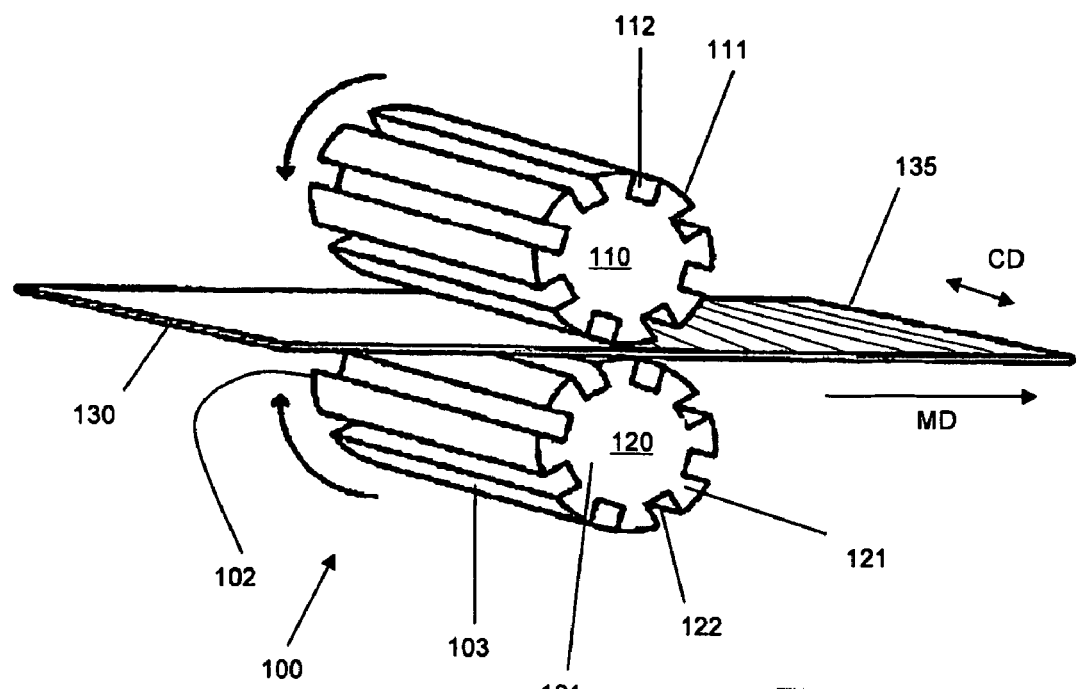
FIG. 1 is a perspective view of a pair of activation rolls.

"Absorbent article" means an article that is capable of absorbing and storing liquid. A "wearable absorbent article" is a device that is placed against or in proximity to the body of a wearer to absorb and contain exudates that may be discharged from the body. Non-limiting examples of wearable absorbent articles include diapers and training pants.

"Activation" is the mechanical deformation of an extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to an extensible material typically results in the extensible material deforming plastically, while the elastic material returns substantially to its original dimension. "Activated" means a material that has been subjected to an activation process.

"Complementary" means the three-dimensional surface features of two rolls are configured to be relative opposites of one another when the surface features overlap. For example, complementary surface features include a raised portion on a first roll that fits into the lowered portion of a second roll (and vice versa) when the surface features are brought into close proximity of one another.

"Direction of activation," means the direction, at any location on an activation roll between two intermeshing surface features, that is substantially perpendicular to the length direction of the intermeshing surface features. For intermeshing surface features that are parallel to each other, the direction of activation is perpendicular to the length direction of both these surface features. For intermeshing surface features that are not parallel to each other, the direction of activation is the average of the two directions that are perpendicular to the length directions of each of the intermeshing surface features. For example, surface features in the form of teeth and grooves that extend in the CD may provide activation in the MD, while surface features in the form of peaks and channels extending in a direction orthogonal to the axis of rotation of the roll may provide activation in the CD. In other examples, the surface features on the activation roll may be configured to activate the web in a continuous curvilinear direction (i.e., no gaps are present to separate the surface features into discrete regions of activation) or a diagonal direction. As disclosed herein, activation in a continuous curvilinear direction is considered a single direction of activation. However, in certain embodiments, activation in an intermittent curvilinear direction (i.e., breaks or gaps are present to separate the surface features into discrete regions of activation) may be considered different directions of activation. A break or gap is a spatial separation between two regions of activation where the shortest dimension in the break or gap, as measured between adjacent surface features, is greater than the smallest pitch of the three-dimensional surface features in the discrete regions of activation separated by the break or gap. When the adjacent surface features are the same height, then the gap size is the peak-to-peak distance between the tips of the surface features. If the adjacent surface features are not the same height, then the gap size is the shortest distance between the tip of the shortest surface feature and a point at the same relative height on the adjacent surface feature.

"Disposed" means the relative position of an element with regard to another element. For example, a first element(s) that is formed (joined and positioned) in a particular place or position as a unitary structure with a second element or as a separate first structural element joined to a second structural element, the first element may be said to be disposed on the second element.

"Elastic" materials are materials that, upon application of a biasing force, can stretch to an elongated length of at least about 150% or even to 200% of its relaxed, original length (i.e. can stretch to 50% or even 100% more than its original length), without rupture or breakage. Further, upon release of the applied force, the material may recover at least about 40%, at least about 60%, or even at least about 80% of its elongation. For example, a material that has an initial length of 100 mm can extend at least to 150 mm, and upon removal of the force would retract to a length of 120 mm (i.e., exhibiting a 60% recovery).

"Extensible" materials are materials that upon application of a biasing force, can stretch to an elongated length of at least about 150% or even 200% of their relaxed, original length (i.e., can stretch to 50% or even 100% more than its original length), without rupture or breakage. Further, upon release of the applied force, the materials show little recovery, for example less than about 40%, less than about 20%, or even less than about 10% of their elongation. For example, a material that has an initial length of 100 mm can extend at least to 150 mm, and upon removal of the force would retract to a length of 140 mm (i.e., exhibiting a 20% recovery).

"Intermesh" means complementary features that mesh together in an overlapping fashion, but do not interlock or substantially constrain the motion of one another.

"Joined" means configurations whereby an element is directly secured to another element by affixing the element directly to the other element, and configurations whereby an element is indirectly secured to another element by affixing the element to an intermediate member(s) that in turn are affixed to the other element.

The "machine direction" or "MD" is the direction that is substantially parallel to the direction of travel of the web as it is activated. Directions within 45 degrees of the MD are considered to be machine directional. The "cross direction" or "CD" is the direction substantially perpendicular to the MD and in the plane generally defined by the web. Directions within 45 degrees of the cross direction are considered to be cross directional.

"Nonwoven" means a porous, fibrous material made from continuous (long) filaments (fibers) and/or discontinuous (short) filaments (fibers) by processes such as, for example, spunbonding, meltblowing, carding, and the like. Nonwovens do not have a woven or knitted filament pattern. Nonwovens may be liquid permeable or impermeable.

"Outboard" and "inboard" mean, respectively, the location of an element relative to a second element with respect to the radial centerline of an activation roll. For example, if element A is outboard of element B, then element A is further from the radial centerline than is element B.

"Stretchable" materials are materials that upon application of a biasing force, can stretch to an elongated length of at least about 150% or even 200%. Stretchable materials may be elastic or extensible depending on the amount of recovery. An example of a stretchable material includes an extensible polypropylene nonwoven joined to an elastic polyethylene film.

"Three-dimensional surface feature" means an element of an activation roll that extends outwardly or inwardly from the roll, and is configured to intermesh with a complementary three-dimensional surface feature of another activation roll to activate a web. Nonlimiting examples of three dimensional surface features include teeth, grooves, peaks, channels, and corrugations.

"Web" means a material capable of being wound into a roll. Webs may be film webs, nonwoven webs, laminate webs, apertured laminate webs, etc. The face of a web refers to one of its two dimensional surfaces, as opposed to its edge. The term "composite web" refers to a web that comprises two or more separate webs that are bonded in a face to face relationship. The bonding can be through the edges of the component webs, although the component webs lie in a face to face relationship with each other.

"X-Y plane" means the plane defined by the MD and CD of a moving web or the length and width of a piece of material.

Apparatus

It is believed, without being limited by theory, that the amount of localized stress applied to a web in regions of the web where the direction of activation changes abruptly (e.g., from CD activation to MD activation in adjacent areas of the web) may be high enough to undesirably damage the web during the activation process. The damage to the web may even be severe enough to render the web commercially unsuitable for its intended use (e.g., excessive pinholing, tearing, thinning, and/or weakening). In the areas of the web where the direction of activation changes abruptly, there may be insufficient space between the three-dimensional surface features present on the activation rolls for the web to occupy as it is being stretched and deformed by the activation process. Spatially separating the areas of activation may solve the problem of web damage, but then the material may lose some or even all of its elastic properties in the areas bordering the nonactivated area because the nonactivated portions of the material may undesirably constrain the stretch properties of the adjacent activated portions. The loss of stretch in one or more portions of the web may detract from the desired properties of the web, e.g., cloth-likeness, softness, stretchability. Surprisingly, it has been found that by placing a suitable buffer region between regions on the roll that provide different directions of activation, the undesirable damage to a web may be minimized or even eliminated during activation without causing undesirable stretch "lock-up."

The apparatus described herein includes a pair of intermeshing activation rolls. The apparatus may be part of a larger manufacturing process, for example, a diaper manufacturing process, or the apparatus may be a stand-alone device for activating a web. The rolls may vary in size, for example, from between 200 to 800 mm in diameter. The rolls may be configured to have three-dimensional surface features such as, for example, teeth, grooves, peaks, channels, corrugations, and the like. The rolls may each include a single surface feature, a plurality of surface features, a single region of surface features, or multiple regions of surface features. The rolls and their respective surface features may be formed from a unitary piece of material, or the surface features may be formed from discrete pieces of the same or different materials and permanently or temporarily joined (e.g., removably and/or reattachably) to the roll before, during, and/or after formation of the rolls. The rolls and the surface features may be made from the same or different materials, and may include any suitable material known in the art. The three-dimensional surface features may be configured to activate two or more portions of a web in different directions simultaneously when the web is fed into a nip formed by the rotating rolls. The term "simultaneously," as used herein with regard to activating a web in different directions, means that the activation process is accomplished using a single pair of rolls, as opposed to a sequential operation which may use two or more pairs of rolls to provide two or more different directions of activation. In contrast to known methods of stretching one or more portions of a web in multiple directions such as, for example, by biaxial activation and/or embossing, each discrete region of activation of the web, when activated by the process described herein, is activated in a single direction as opposed to the two or more directions of activation provided by other processes. It is believed, without being limited by theory, that limiting the direction of activation in a particular region of a web to a single direction may reduce the likelihood of damage to the web during the activation process. Another difference between embossing, which is typically used to provide an image on a web as opposed to providing increased extensibility, and activation is that during an embossing process the material that is embossed occupies substantially all of the space between the male and female portions of the embossing pattern on the two rolls. During activation, however, the material being activated is stretched between two intermeshing three-dimensional surface features, one on each of the two rolls, but does not occupy all of the space between these intermeshing surface features.

In certain embodiments, it may be desirable to activate one or more portions of a web in the MD. MD activation may be accomplished by configuring one or more portions of each roll to include teeth that extend parallel to the axis of rotation of the rolls. The roll will typically include grooves disposed between adjacent teeth. The teeth and grooves may be disposed on the activation roll such that they activate only the portion of the web where MD activation is desired, for example, along one or more of the longitudinal sides of the web and less than, for example, 60 mm, 40 mm, 20 mm, 10 mm, or 5 mm inboard of the longitudinal side edge. The dimensions of the portion of a roll that includes the teeth and grooves may be varied, as desired. In certain embodiments, it may be desirable to activate one or more portions of a web in a direction other than the MD, e.g., the CD. Activating a web in the CD may be accomplished by providing three-dimensional surface features that include peaks extending perpendicular to the axis of rotation of the rolls. The surface features will typically include channels disposed between adjacent peaks. The peaks and channels may be disposed on the rolls so that they activate only the portion of the web where CD activation is desired, for example, inboard of the MD activated portions. While this example discloses MD and CD activation, it is to be understood that the rolls may be configured to provide other directions of activation including, without limitation, diagonal and/or curvilinear directions of activation.

The three-dimensional surface features may have a "pitch," which is the distance between the same relative points on the tips of two adjacent surface features of the same type (e.g., the tip-to-tip distance between two adjacent raised portions). The pitch may be varied as desired to provide a suitable level of activation. Surface features having a lower pitch typically provide more activation to a material, for the same depth of engagement, than surface features having a higher pitch (i.e., impart greater extensibility to the activated material). Suitable pitch values for the surface features disclosed herein include between 1 and 10 mm, 2 and 8 mm, or 3 and 7 mm. In certain embodiments, the pitch between two surface features may vary depending on which points on the surface features are chosen to determine the distance between the tips, e.g., nonparallel surface features configured to provide a curvilinear direction of activation. In such instances, the pitch is determined by measuring the distance between the midpoints of the tips of the surface features. The surface features may also have a height, which is the distance from the surface of the roll to the tip of the surface feature, of between 2 and 20 mm. The tips of surface features may be flat or rounded. Rounded tips may place less stress on a web. The tips of the surface features described herein may have a relatively high aspect ratio, i.e., the length of the tip is substantially larger than the width. For example, the aspect ratio may be greater than 10, or even greater than 100. The width of a particular surface feature may be, e.g., less than about 2 mm, less than 1 mm, or less than 0.5 mm.

In certain embodiments, particular portions of a web may be activated in a first direction (e.g., the MD, CD, or a curvilinear direction) by a particular region of an activation roll. Other portions of the web, which are spatially separated by a buffer zone from the particular portion of the web activated in the first direction, may be activated in a second direction. Still other portions of the web, which are spatially separated by a buffer zone from the particular portions of the web activated in the first and second directions, may be activated in a third direction, and so on as desired. The intermeshing activation rolls may include at least one buffer region on one or both of the rolls for separating various regions of the rolls configured for activating a web in different directions, the buffer regions may correspond to buffer zones on the activated web. A buffer region may include no three-dimensional surface features, relatively few three-dimensional surface features, or modified three-dimensional surface features (e.g., teeth having a lower tooth height than other teeth on the same roll). In embodiments where the buffer region includes three-dimensional surface features, the surface features provide little or even no activation. For example, the surface features may include teeth or peaks that do not provide a sufficient depth of engagement or proper orientation to activate a web passing between the rotating rolls. It is believed, without being limited by theory, that the portion of the web that corresponds to the buffer region on the roll may absorb at least some of the energy exerted by the activation rolls on the web during a multi-directional activation process and thereby reduce or even prevent the material failure that may be associated with simultaneous multi-directional activation.

The buffer region may be any suitable size as long as the activated web is not substantially damaged as a result of activation and the extensibility of the activated portion of the web is not undesirably locked up by a nonactivated buffer zone. The buffer region may be contiguous with the boundary of one or more "regions of activation" on an activation roll (i.e., discrete portions of the activation roll that include three-dimensional surface features configured to activate a web), and/or may partially or completely surround one or more regions of activation. The buffer region may extend in one or more of the CD, MD, a curvilinear direction or a diagonal direction. The width of the buffer region is determined the same way as the gap size mentioned above, except that the adjacent surface features used in the measurement are configured to provide activation in different directions. Suitable examples of buffer region widths include widths of between 2 and 30 mm, 4 and 20 mm, or 6 and 10 mm. The width of a buffer region may or may not be constant throughout the same buffer region. When an activation roll includes more than one buffer region, the buffer regions may be the same width(s), but need not necessarily be so. It is to be understood that a buffer region spatially separates discrete portions of an activation roll configured to activate a web in different directions (e.g., CD and MD, CD and curvilinear, MD and curvilinear, MD and diagonal, and any combination of these). Discrete portions of a roll which are configured to activate a web in the same direction (e.g., MD and MD, CD and CD, curvilinear and curvilinear, diagonal and diagonal), but which are spatially separated from one another (e.g., to provide intermittent activation in the same direction) are not separated by a buffer region, as contemplated herein. Discrete portions of an activation roll configured to activate a web typically have a surface area of $>50$ mm$^2$, e.g., $>5000$ mm$^2$, or $>50000$ mm$^2$. The surface area of a region of activation is determined by measuring the surface area of the corresponding activated area on a web activated by the roll. While there is no absolute upper limit for the size of the particular area to be activated, it is limited to less than 100%, e.g., <90%, <80%, <70, or even <60%. For example, an activation roll used for activating an outer cover for use in a disposable diaper or training pant may include two MD regions of activation that have a combined total surface area of 100 cm$^2$ for activating the leg band portions of the outer cover, and one CD region of activation that has a total surface area of 900 cm² for activating a body portion of the outer cover.

The three-dimensional surface features of the matched activation rolls described herein are typically configured to intermesh. That is, the three-dimensional surface features of one roll may be designed to operatively engage the three-dimensional surface features of the other roll such that the material to be activated, the rolls, and/or the three-dimensional surface features are not undesirably damaged when the rolls rotate and the material is passed between the rotating pair of rolls. In certain embodiments, where the rolls include raised portions (e.g., teeth) separated by lowered portions (e.g., grooves), which extend along the roll in a direction parallel to the axis of rotation of the roll, the raised portions of one roll may be configured to fit into (i.e., mesh) with the lowered portions of the other roll, and vice versa. In this way, the rolls, when rotated, may pass a web through a tortuous, "zig-zag" path created by the intermeshing teeth and grooves, thereby activating the web in the MD. Activation in the CD may be accomplished by configuring an intermeshing pair of rolls to have, e.g., peaks and channels that extend perpendicular to the axis of rotation of the rolls. In certain embodiments, the intermeshing peaks and channels may be described as an alternating stack of two different diameter disks. Disks with a larger diameter are alternated on the rolls with disks that are smaller in diameter. The intermeshing pair of rolls is aligned so that the larger diameter disks of one roll are opposite the smaller diameter disks of the other roller. In this way, the peaks and channels that extend perpendicular to the axis of rotation of the rollers intermesh.

A drive motor or other prime mover is typically utilized to drive at least one of the rolls ("driven roll"). In embodiments where the activation rolls include surface features in the form of intermeshing teeth and grooves that extend in a direction parallel to the axis of rotation and where the intermeshing rolls remain in constant engagement (i.e., the intermeshing surface features are disposed around a substantial portion of the circumference of the rolls), the second roll typically need not be driven because torque will be transferred from the driven roll through the web to the second roll. It may be desirable to configure the raised portions of the rolls so that they do not contact one another in a typical activation operation. It is to be understood, however, that one or more drive motors or other prime movers may be used to drive one or both of the rolls. In addition, the rolls may each be mounted on a shaft that is positioned between two machine side plates. The first shaft may be located in fixed bearings while the other second shaft is located in bearings in slidable members such that the position of the slidable members is adjustable, e.g., by means of adjusting screws or other devices known in the art. The adjusting device moves the slidable member, and thus the movable roll, respectively toward or away the stationary roll to further engage or disengage the gear-like teeth of the pair of intermeshing rolls. The depth of engagement of the roller teeth typically determines the degree of elongation to which the web is subjected. A balance is typically drawn between the depth of engagement of the roller teeth and the web composition, as these may affect the physical properties of the activated web.

FIG. 1 shows an example of an apparatus 100 that includes a pair of rotatable activation rolls 110 and 120. The rolls 110 and 120 may include intermeshing teeth 111 and 121, opposing side edges 101 and 102, and a radial centerline 103 that extends through the radius of the roll 110 or 120. The teeth 111 of the upper roll 110 are configured to fit into (i.e., mesh) with the grooves 122 of the lower roll 120 when the rolls rotate in opposite directions (i.e., clockwise and counter-clockwise, respectively, as indicated by the arrows). Likewise, the teeth 121 of the lower roll are configured to fit into with the grooves 112 of the upper roll 110. A web 130 may be passed through the rolls 110 and 120 in the MD to produce an activated web 135. In this example, the teeth 111 and 121 are shown as being coextensive with the rolls 110 and 120 in the CD, however, it is to be understood that the teeth need not necessarily extend along the entire length of the roll, but may be configured to extend any distance on the roll 110 and/or 120, as desired.

Figure 2:
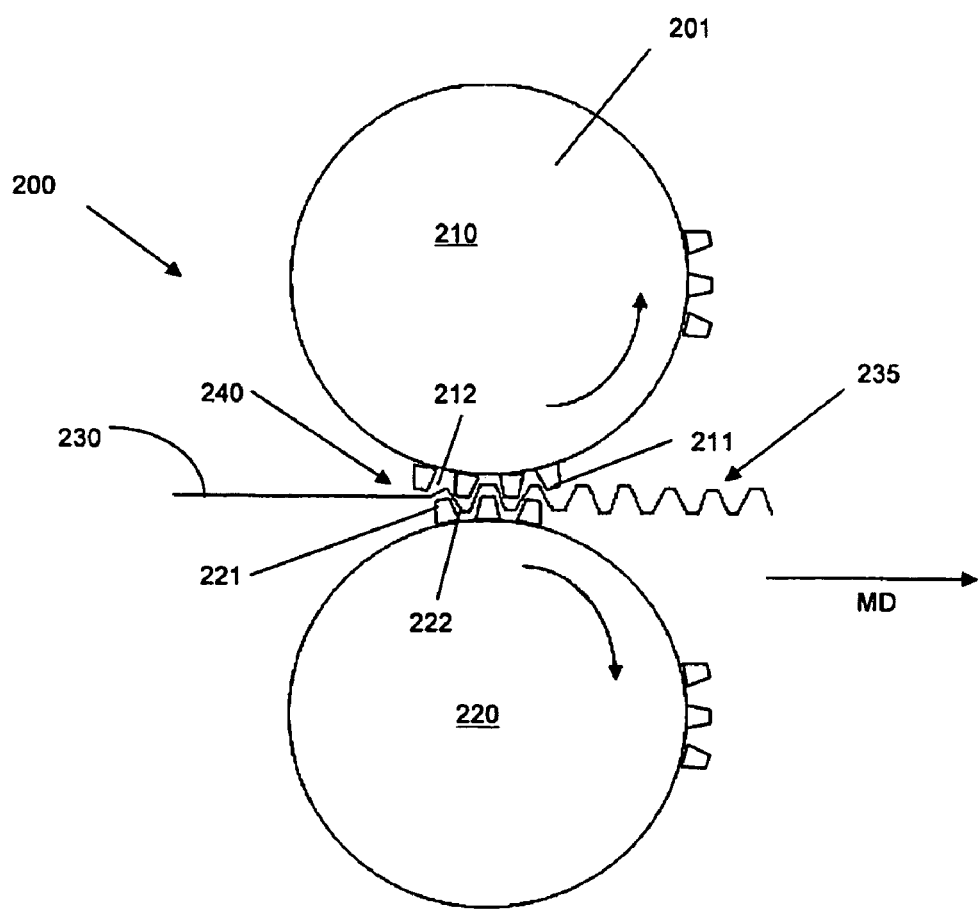
FIG. 2 is a side view of a pair of activation rolls.

FIG. 2 shows an example of an apparatus 200 that includes a pair of rotatable rolls 210 and 220 having intermeshing teeth 211 and 221. As can be seen in FIG. 2, the teeth 211 of the upper roll 210 are configured to fit into the grooves 222 of the lower roll 220, and the teeth 221 of the lower roll 220 are configured to fit into the grooves 212 of the upper roll 210 when the rolls 210 and 220 rotate. A web 230 may be fed into the nip 240 formed between the rotating rolls 210 and 220. As used herein, "nip" means the region where the surfaces of the two rolls 210 and 220 overlap or begin to overlap to receive and move the web 230. After passing between the intermeshing three-dimensional surface features (211, 212, 221, and 222) of the rolls 210 and 220 in the MD, the web 230 is activated and may have corrugations 235 or other visible characteristics indicative of activation.

Figure 3:
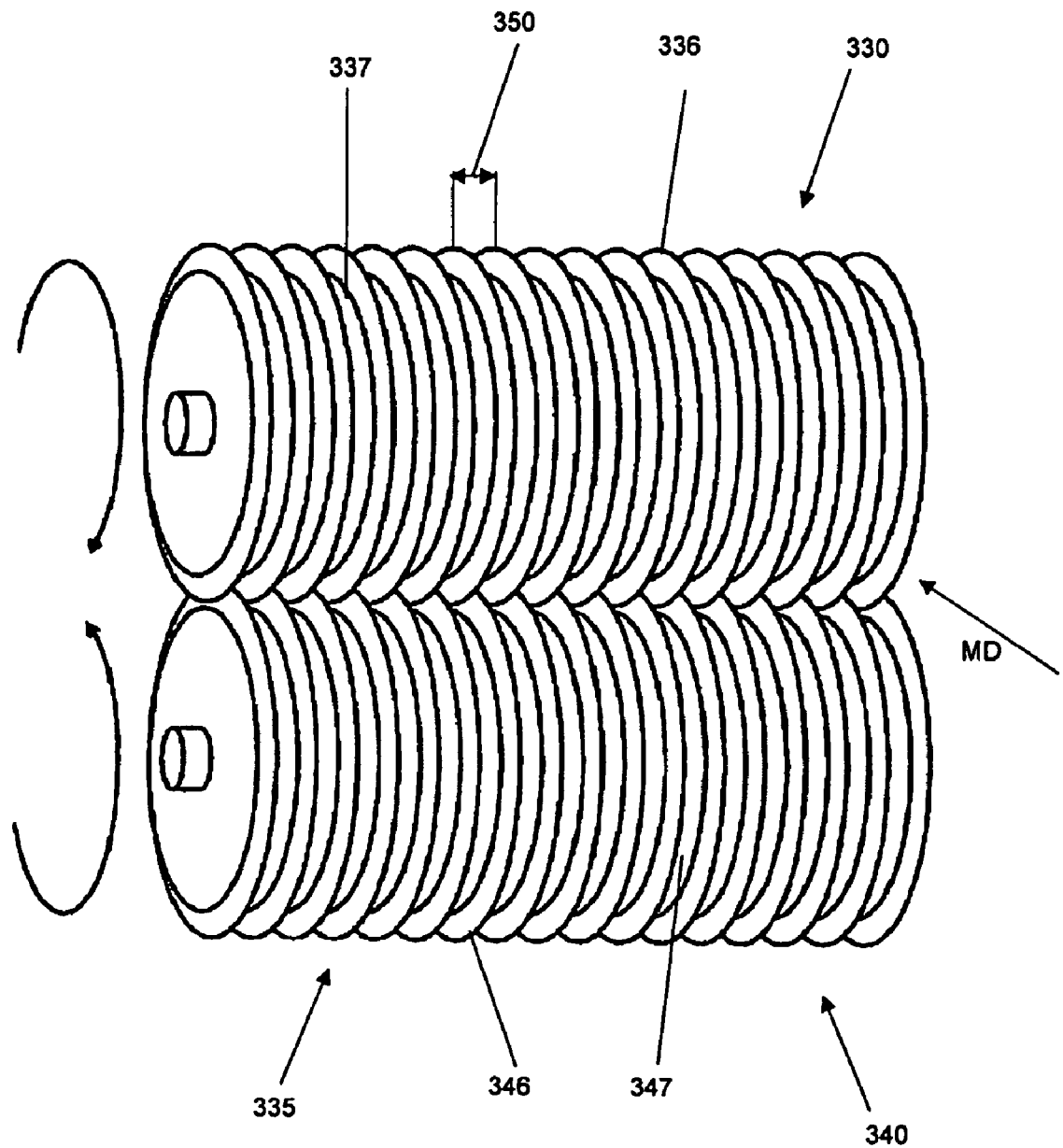
FIG. 3 is a perspective view of a pair of activation rolls.

FIG. 3 shows an example of a pair of rotatable rolls 330 and 340 that may be suitable for activating a web in the CD. Each roll 310 and 320 may include three-dimensional surface features 335 configured as an alternating series of peaks 336, 346 and channels 337, 347 that form an overall corrugated surface. The exact configuration, spacing and depth of the channels 337, 347 may vary, depending on, for example, the amount of elasticity desired in the activated portion of the fully processed web. In certain embodiments, a pitch 350 of approximately 3.8 mm, an included angle of approximately 12° as measured at the peak, and a peak-to-groove valley depth of approximately 7.6 mm may be suitable. When the corrugated rolls are adjusted so that their opposing peaks 336, 346 overlap one another to a depth of between, for example, 2 mm and 10 mm, 5 mm and 7 mm, or 3.8 mm and 4.4 mm, good extensibility characteristics may be produced in a web. The degree of overlap of the opposing peaks 336, 346 (i.e., the "depth of engagement") on the aforementioned corrugated rolls 330, 340 may be adjusted, as desired, to produce more or less extensibility in the activated portion of the web. For the aforementioned roll geometry and laminate web construction, peak-to-peak overlap depths ranging from as little as 1.27 mm to as much as 5.71 mm may be achieved.

Figure 4:
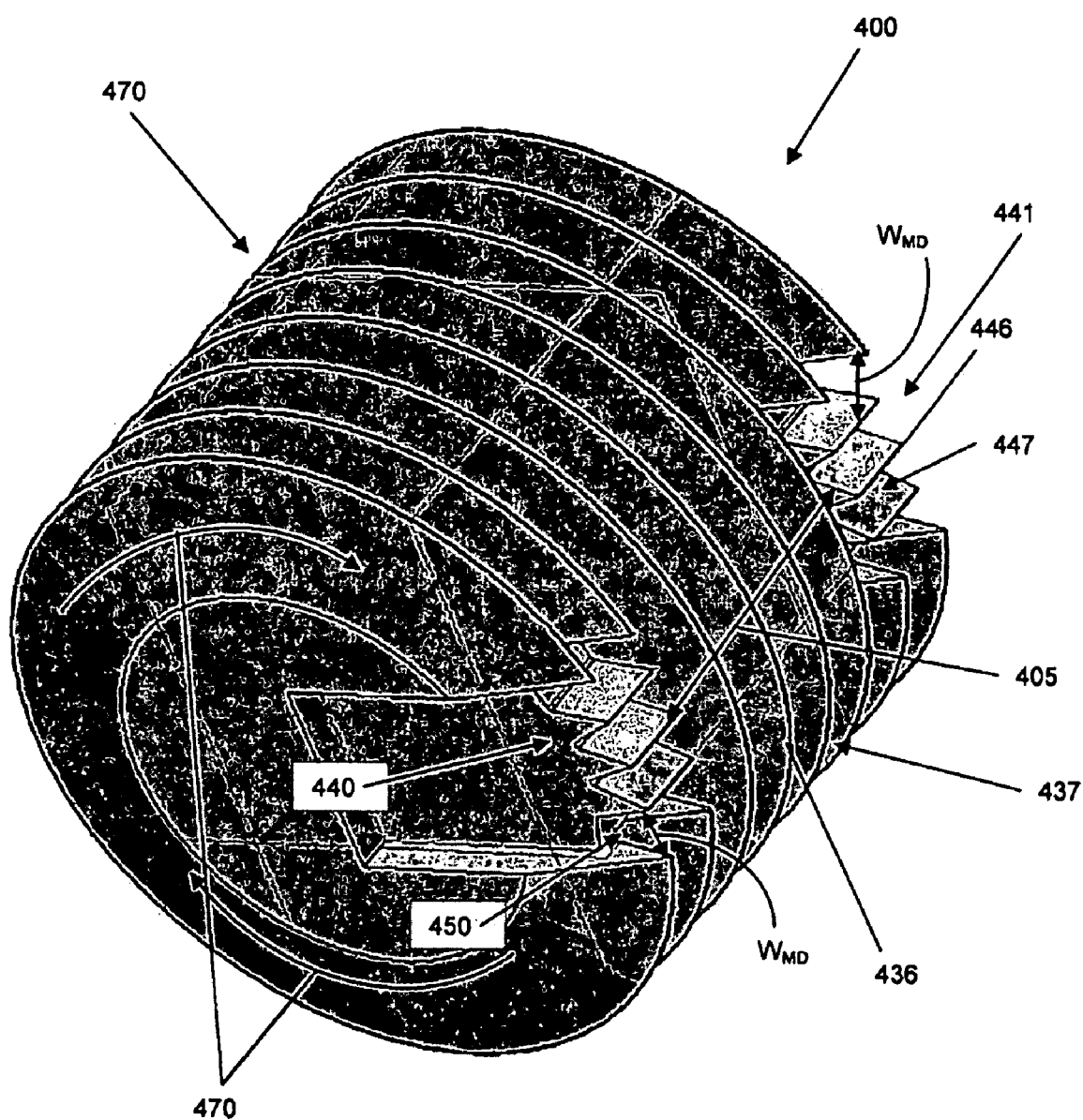
FIG. 4 is a side perspective view of an activation roll.
Figure 5:
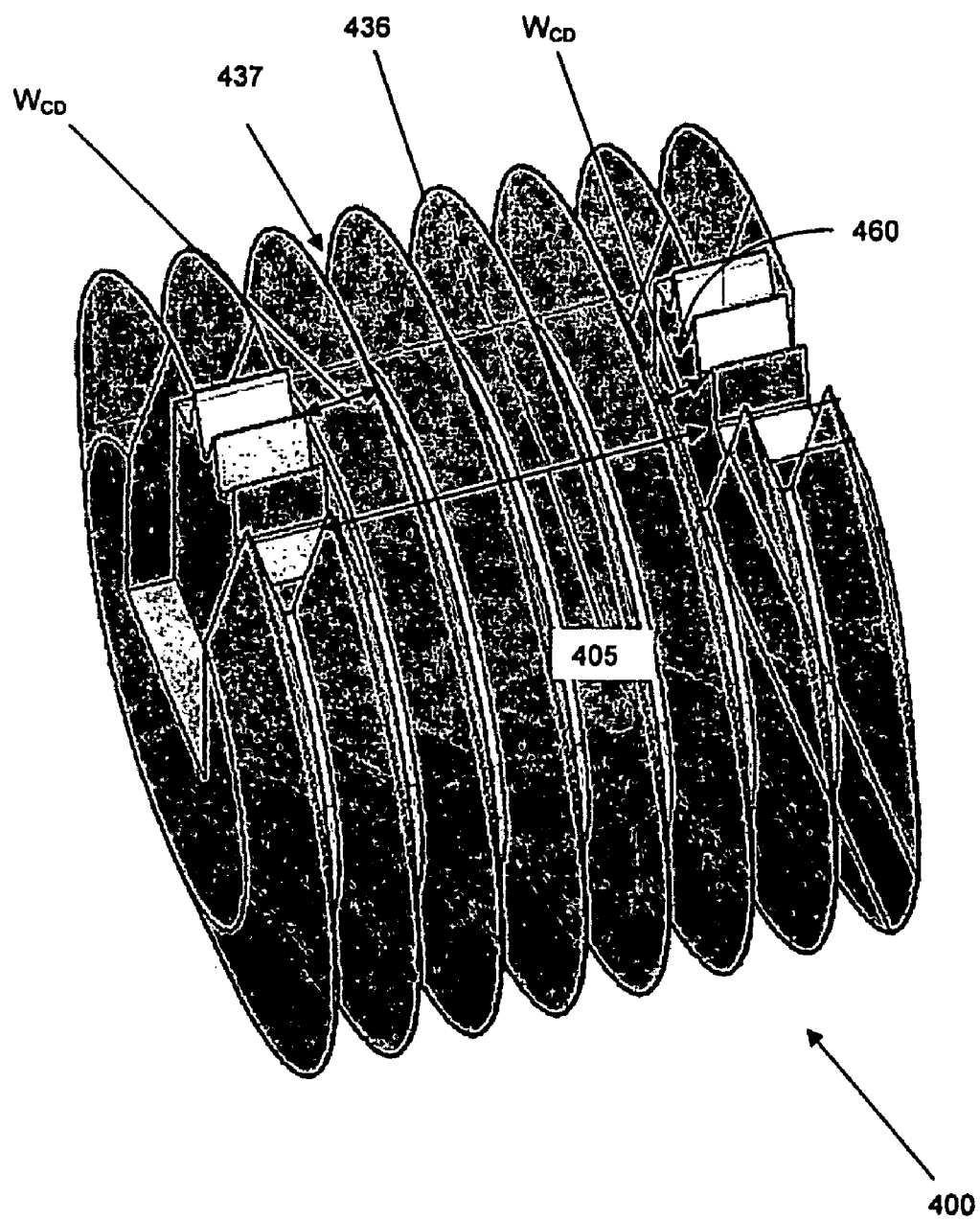
FIG. 5 is a front perspective view of an activation roll.
Figure 6A:
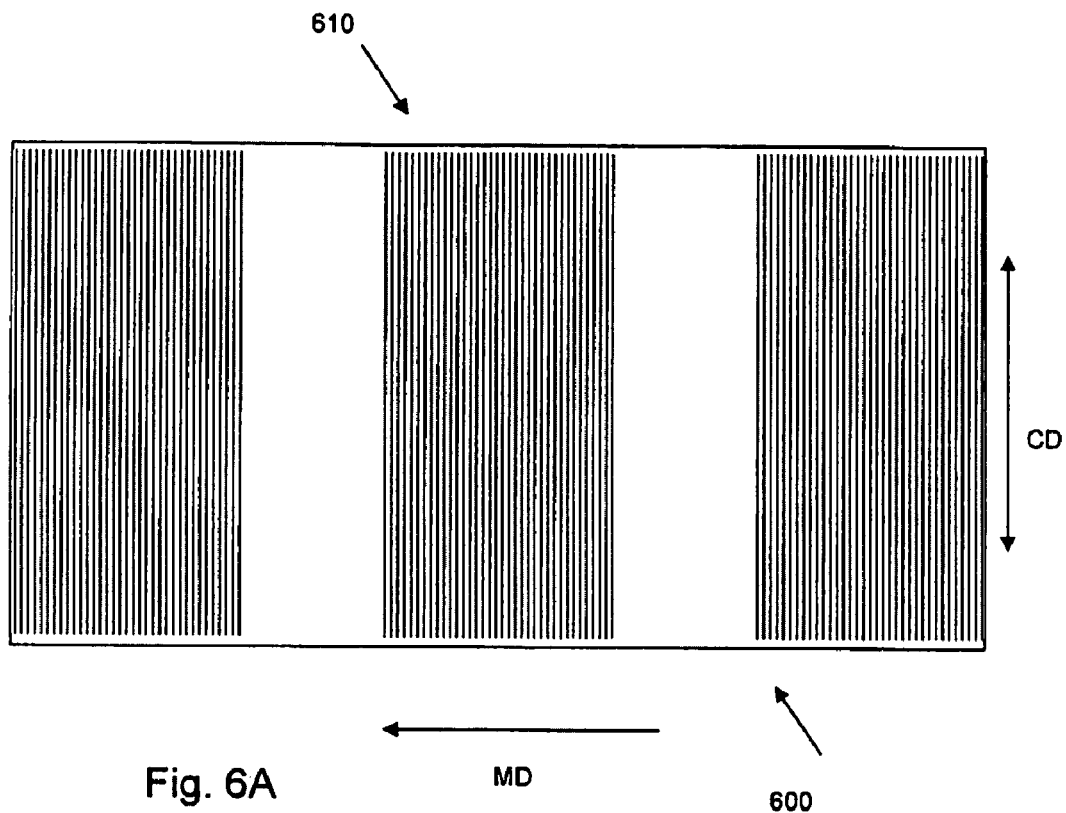
FIGS. 6A-6C are plan views of examples of activated webs.
Figure 6B:
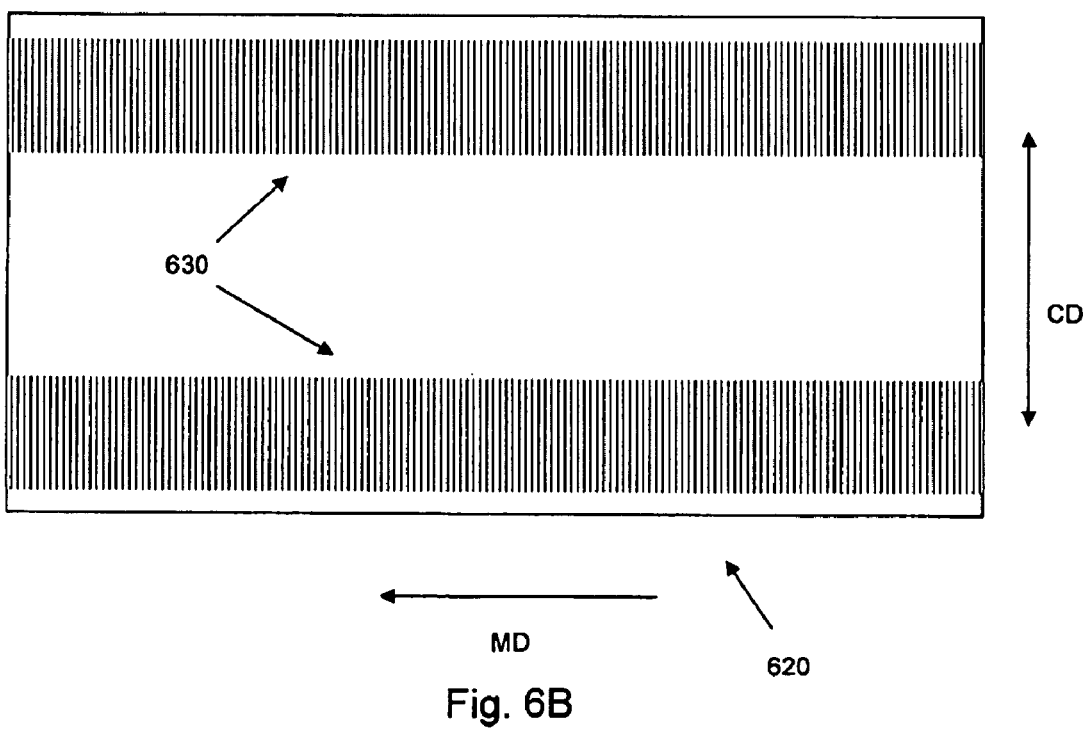
Figure 6C:
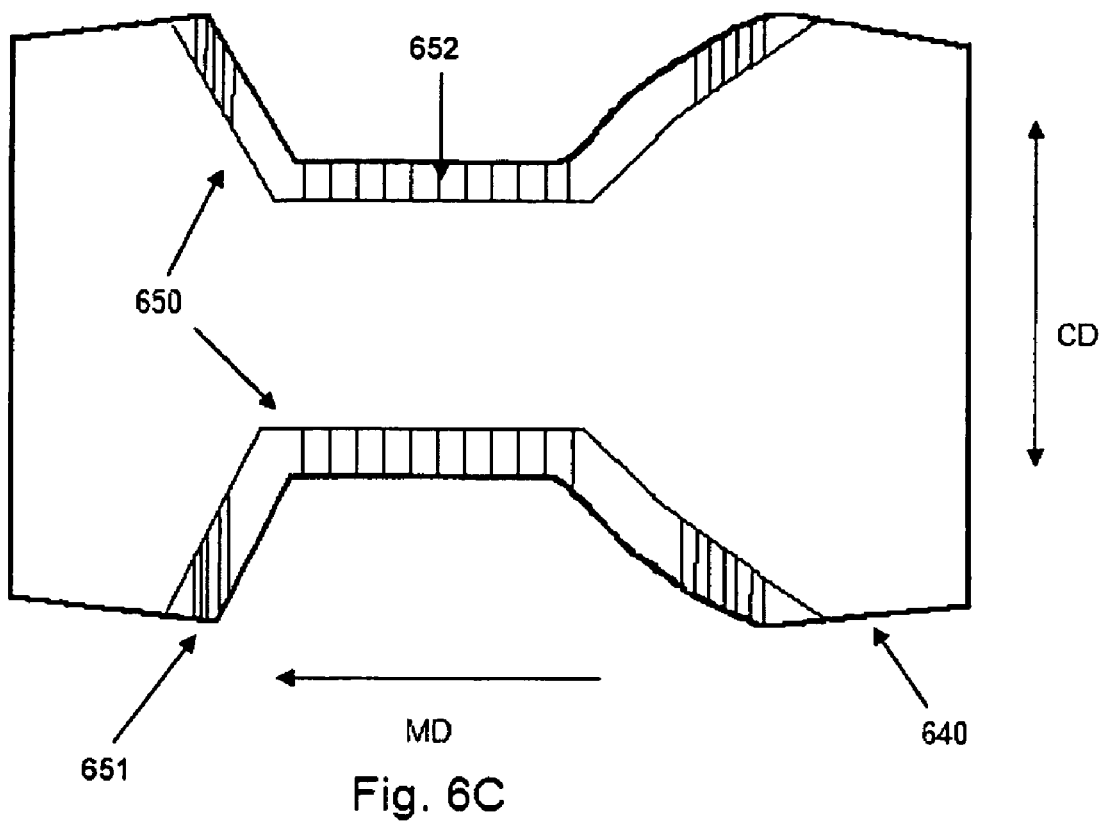

FIGS. 4-5 show perspective views of an example of a roll 400 that includes three-dimensional surface features for activating a web in two different directions. The roll 400 may be configured to rotate in the clockwise direction, as indicated by arrows 470. The roll 400 may include three-dimensional surface features in the form of teeth 446 separated by grooves 447 between the teeth 446. While not shown, it is to be understood that the roll 400 is one roll of a pair of intermeshing matched rolls, and that the second roll in the pair will have surface features which complement the surface features of the roll 400 shown in FIGS. 4-5. The pitch of the teeth 446 may be the same for all teeth 446 on the roll 400 or different, depending on the location, amount, rate, and direction of activation desired. The teeth 446 and the grooves 447 between the teeth 446 may be configured to extend across the roll 400 in a direction parallel to the axis of rotation so as to provide MD activation to a portion or portions of a web. A single region 440 of teeth 446 and grooves 447 may be configured to activate a particular portion or portions of a web in the MD only one time for each complete revolution of the roll 400 (i.e., 360° of rotation). An opposing region 441 of teeth 446 and grooves 447 may be included on the opposite side, axially, of the roll 400 to provide, e.g., a web having MD activated portions that are symmetrical in the CD. A region 440, 441 may include any number of the same or different sized teeth 446 and grooves 447 suitable for providing the desired activation. A region 440, 441 is distinguished from another region 440, 441 by a discernible spatial separation between the two regions 440 and 441, such as space 405. In certain embodiments, the roll 400 may include one or more regions 440, 441 of teeth 446 and grooves 447 positioned continuously around the entire circumference of the roll 400 so as to provide continuous activation of a moving web in the MD. In certain embodiments, regions 440, 441 of teeth 446 and grooves 447 may be intermittently positioned (i.e., spatially separated) around the circumference of the roll 400 to provide areas of MD activation on a web that are intermittent in the MD. For example, two or more regions 440, 441 of teeth 446 and grooves 447 equally spaced around the circumference of the roll 400, but separated by a break(s) or gap(s), may provide areas of MD activation on a moving web that are equidistantly separated in the MD. FIG. 6A shows an example of a web 600 having MD activated areas 610 that are continuous in the CD and intermittent in the MD. In certain embodiments, regions 440, 441 of teeth 446 and grooves 447 may be spaced apart in the axial direction to provide areas of MD activation on a web that are intermittent in the CD. FIG. 6B shows an example of a web 620 having MD activated regions 630 that are continuous in the MD and intermittent in the CD. In certain embodiments, regions 440, 441 of teeth 446 and grooves 447 may be configured to activate one or more portions of a web intermittently in the MD and CD. FIG. 6C shows an example of a web 640 having MD activated areas 650 that are intermittent in the CD and MD. In addition, particular portions of the web 640 may be activated at higher levels (i.e., have greater extensibility) than other areas that are activated in the same direction. The higher activated areas 651 and lower activated areas 652 may be positioned in any desirable configuration on the web.

Figure 7A:
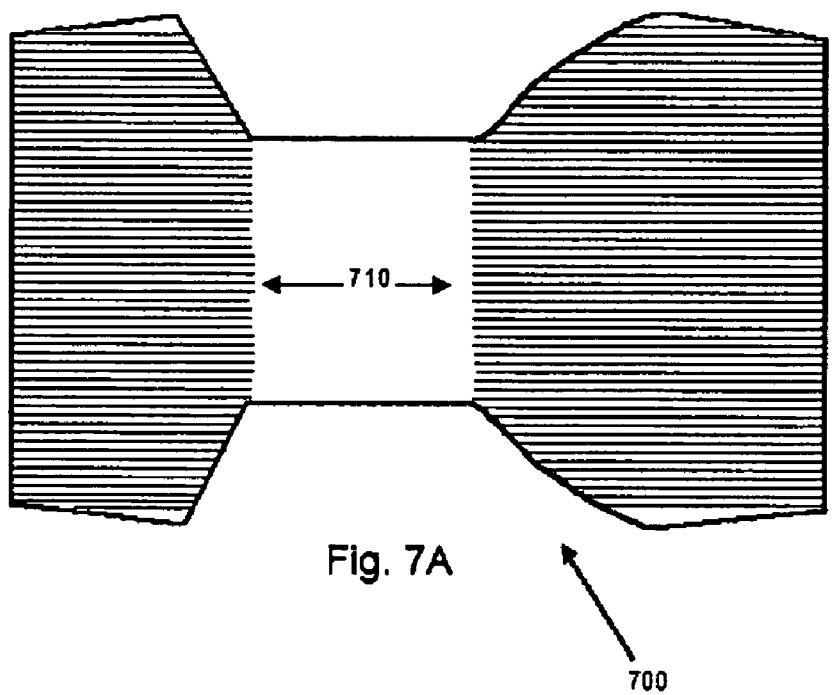
FIGS. 7A-7C are plan views of examples of activated webs.
Figure 7B:
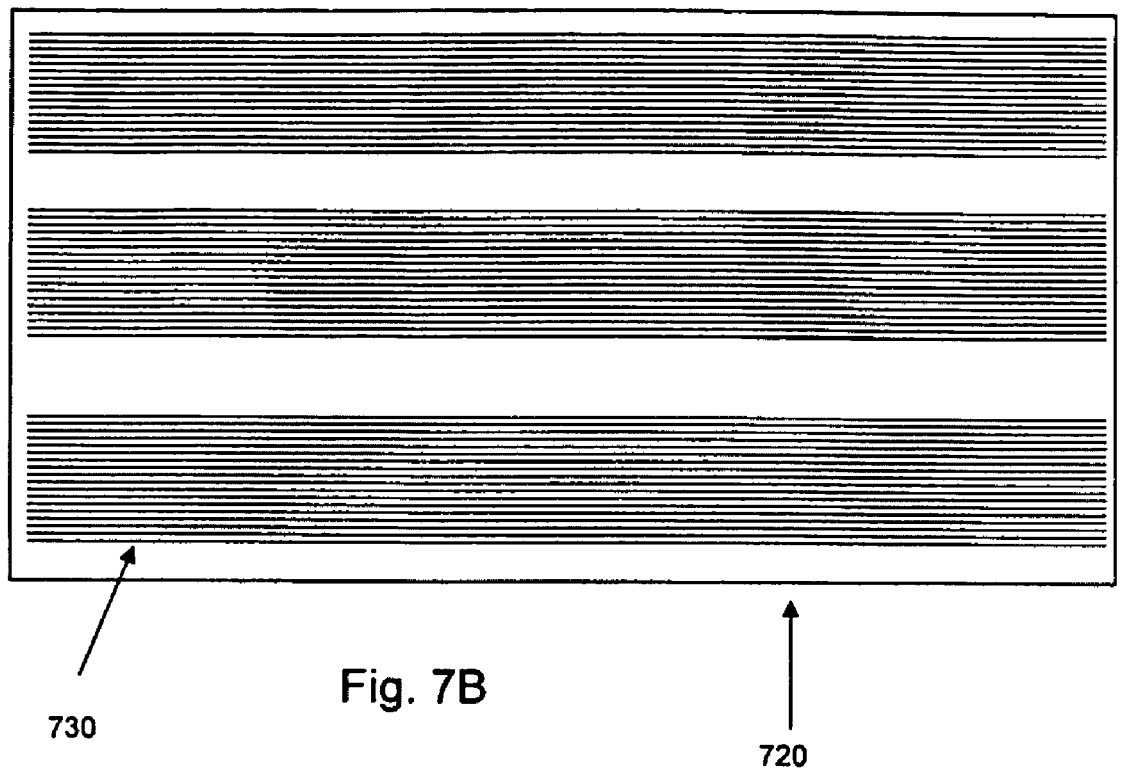
Figure 7C:
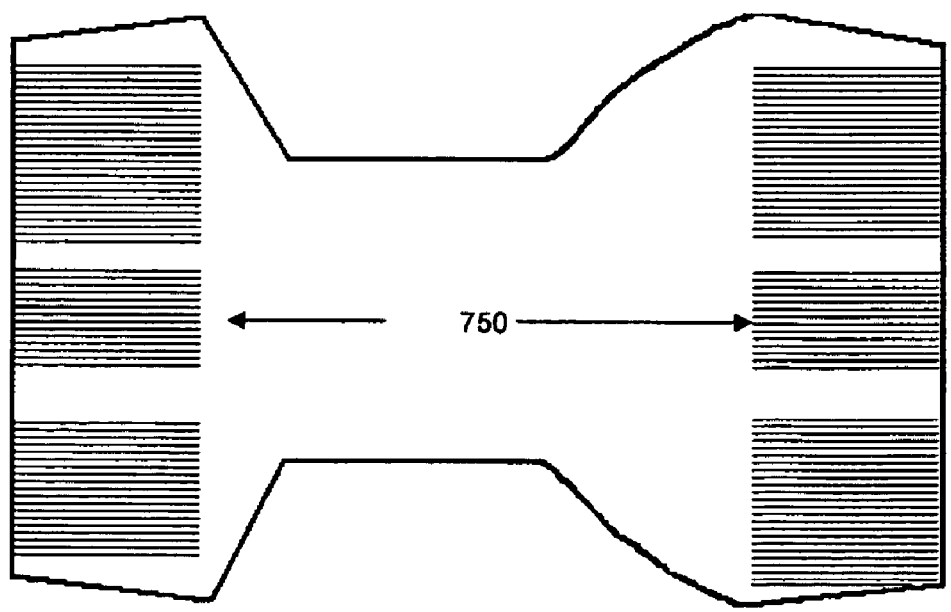

The roll 400 may include three-dimensional surface features in the form of peaks 436 separated by channels 437 between the peaks 436. The pitch of the peaks 436 may be the same for all peaks 436 on the roll 400 or different, depending the location, amount, rate, and direction of activation desired. The peaks 436 and channels 437 may be disposed in a continuous configuration around substantially the entire circumference of the roll 400 in order to continuously activate a particular portion or portions of a moving web in the CD. In certain embodiments, the peaks 436 and channels 437 may be disposed such that they extend only partially around the circumference of the roll 400 in order to provide CD activation once for each complete revolution of the roll 400. In certain embodiments, regions 470 of peaks 436 and channels 437 may be intermittently positioned around the circumference of the roll 400 to provide one or more areas of CD activation on a web that are intermittent in the MD. For example, two or more regions 470 of peaks 436 and channels 437 spaced around the circumference of the roll 400, but separated by a break(s) or gap(s), may provide areas of CD activation on a web that are intermittent in the MD. FIG. 7A shows an example of a web 700 having CD activated areas 710 that are continuous in the CD and intermittent in the MD. In certain embodiments, regions of peaks 436 and channels 437 may be spaced apart in the axial direction to provide areas of CD activation on a web that are intermittent in the CD. FIG. 7B shows an example of a web 720 having CD activated areas 730 that are continuous in the MD and intermittent in the CD. In certain embodiments, regions of peaks 437 and channels 437 may be configured to provide areas of CD activation 750 on a web 740 that are intermittent in the MD and CD, for example, as shown in FIG. 7C.

The roll 400 may include a circumferential buffer region 450 and an axial buffer region 460. The circumferential buffer region 450 may be configured to separate regions of directionally different activation in the axial direction. The circumferential buffer region 450 has a width ($W_{cd}$), which may be, e.g., any value that falls within the range of between 2 and 30 mm. The axial buffer region 460 may be configured to separate regions of directionally different activation extend in the circumferential direction (i.e., around the circumference of the roll 400). The axial buffer region 460 has a width ($W_{md}$), which may be, e.g., any value that falls within the range of between 2 and 30 mm. The axial and circumferential buffer regions 460 and 450 may extend in any direction within 45° of the axial direction or the circumferential direction (as measured in the plane defined by the surface of the roll). The roll 400 may include one or more buffer regions positioned to separate any number of surface features and/or regions of surface features, which are configured to activate a web in different directions.

Figure 8A:
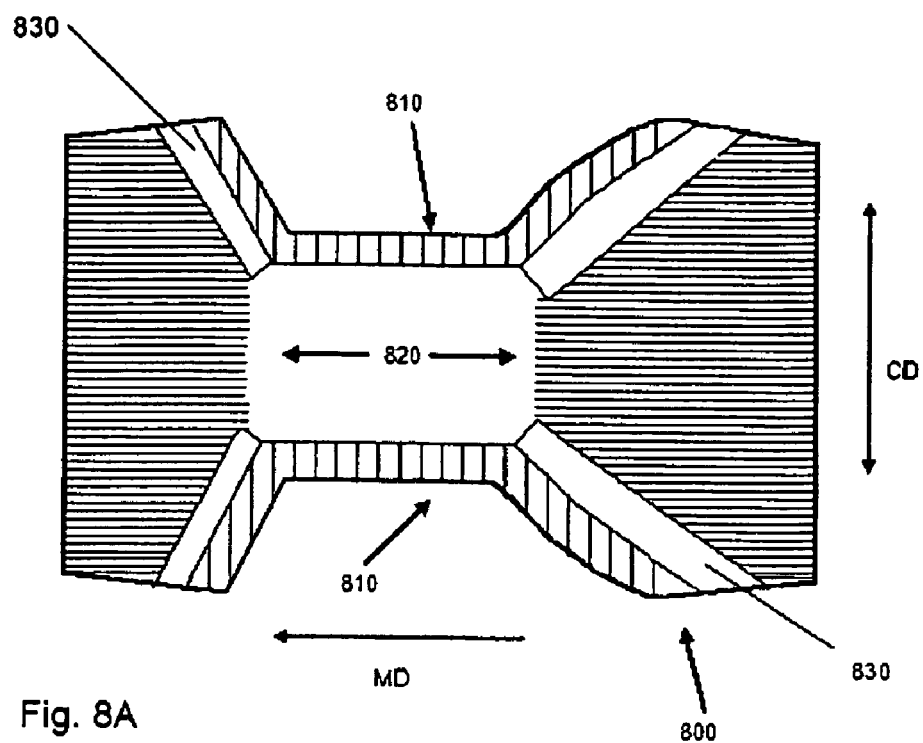
FIGS. 8A and 8B are plan views of an example of an activated web.
Figure 8B:
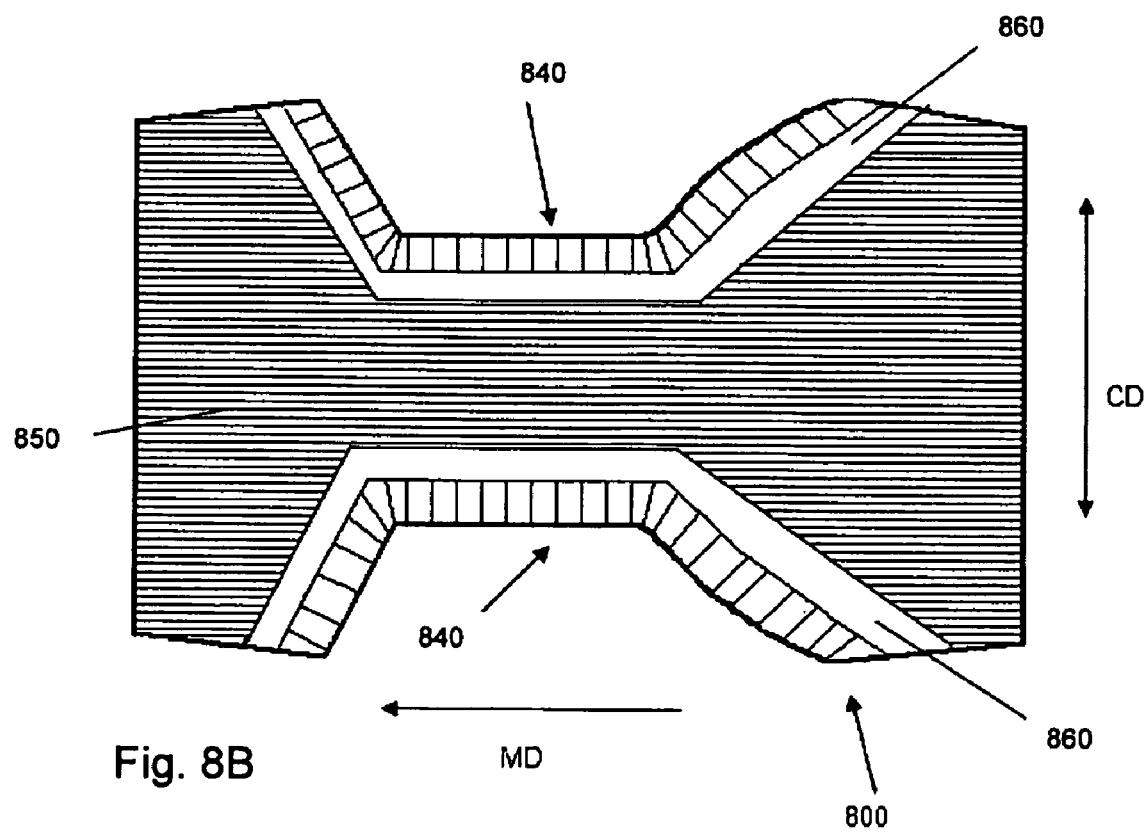

The three-dimensional surface features and the buffer region(s) 450, 460 of the roll 400 may be arranged to provide any suitable configuration of intermittent and/or continuous activation pattern, as desired. FIG. 8A shows an example of a web 800 having MD activated portions 810 that are continuous in the MD and intermittent in the CD, and CD activated portions 820 that are continuous in the CD and intermittent in the MD. FIG. 8A shows the web 800 as including a buffer zone 830 between the CD activated portion 820 and the MD activated portions 810. In certain embodiments, the web 800 may include continuous curvilinear direction activated portions 840, and CD activated portions 850, as shown in FIG. 8B. The curvilinear direction activated portions 840 and the CD activated portions 850 may be separated by a buffer zone 860.

In certain embodiments, an apparatus that includes a pair of intermeshing activation rolls may be configured to activate a particular number of articles and/or a particular number of portions of a single article for each revolution of the activation rolls. The three-dimensional surface features of the rolls may be circumferentially spaced around the roll to activate any number of articles per revolution (e.g., 2, 3, 4, 5, 6, 7, 8, 9, or even 10 or more) and/or any number of portions of a single article (e.g., 2, 3, 4, 5, 6, 7, 8, 9, or even 10 or more). For example, the rolls may be configured as 5-up rolls. In a 5-up configuration, the rolls may include five regions of complementary three-dimensional surface features circumferentially spaced 72° apart around each roll. In such a configuration, the rolls may be capable of activating a continuous moving web up to 5 times in the MD and/or CD for each revolution of the rolls, which may correspond to activating five different articles, five portions of a single article, or any combination thereof. It is to be understood that the number of articles or portions of a single article activated in a single revolution need not necessarily be the same for each revolution. For example, the rolls may be configured to activate four articles or portions of an article in one revolution and five articles or portions of an article in a subsequent revolution. It is to be further understood that the three-dimensional surface features (or regions thereof) may be positioned on the rolls in any suitable configuration to provide the desired number of activations per revolution, and that in embodiments where the rolls are configured to activate a web multiple times in a single revolution, the surface features need not be configured to activate the web at the same rate or the same amount.

Disposable Absorbent Article

Figure 9:
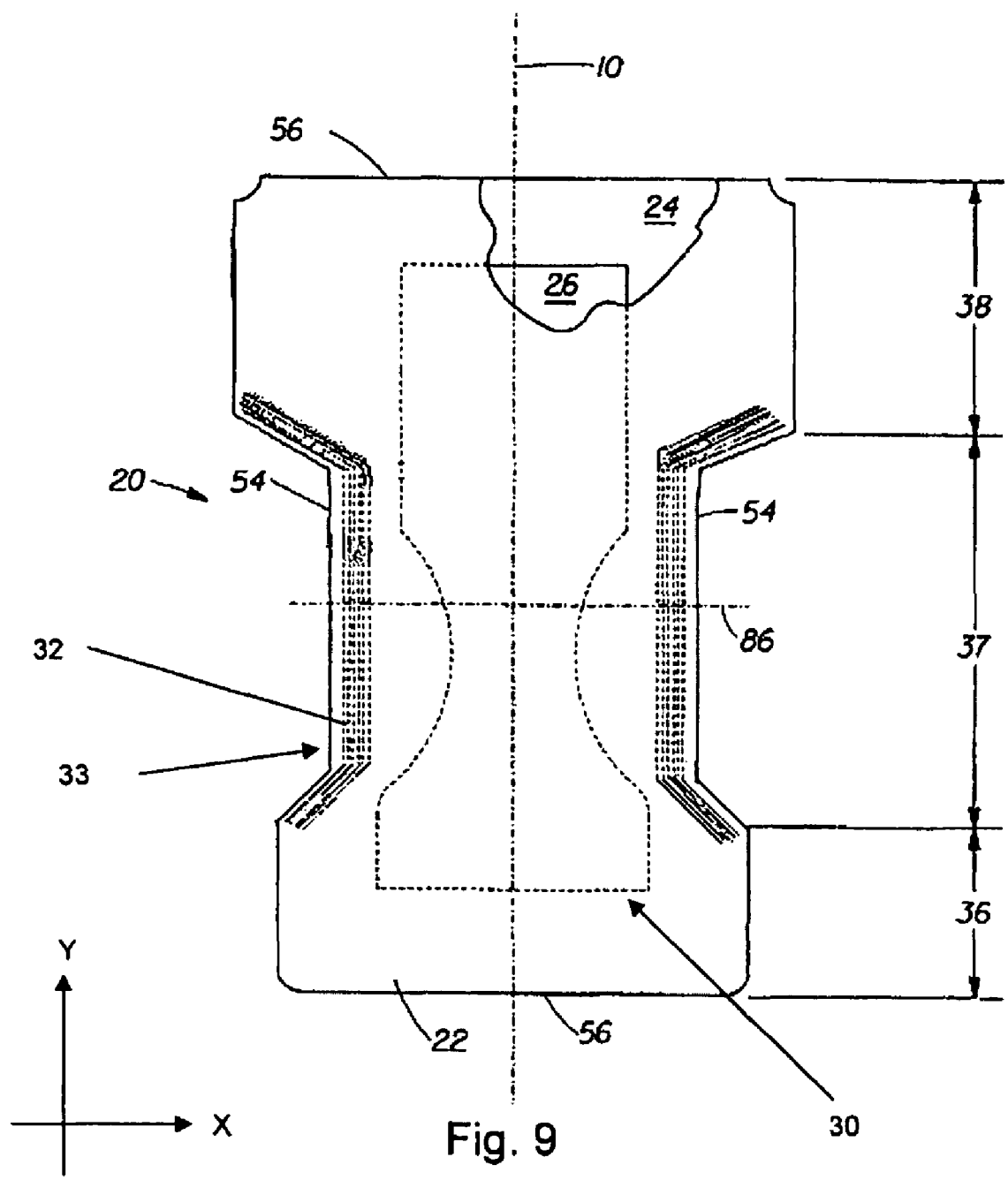
FIG. 9 is a plan view of an example of a disposable absorbent article.

FIG. 9 shows an example of a disposable absorbent article 20 in a flat, uncontracted state. The disposable absorbent article 20 of FIG. 9 may be a wearable article such as a disposable diaper or training pant. The disposable absorbent article 20 may be arranged in a fastened configuration (i.e., the article 20 may be fastenable, refastenable, or prefastened) to form a waist opening and at least one leg opening. The disposable absorbent article 20 may include a longitudinal centerline 10 that extends in the longitudinal direction (Y) and a lateral centerline 86 that extends in the lateral direction (X). The longitudinal and lateral directions may be parallel to the MD and CD, respectively. The disposable absorbent article 20 may include a liquid permeable topsheet 24, an outer cover 22, and an absorbent core 26 disposed between the topsheet 24 and the outer cover 22. The outer cover 22 may include a leg band portion 33. The leg band portion 33 of the outer cover 22 may encircle the entire circumference of the leg opening when the article 20 is in a fastened configuration. The disposable absorbent article 20 may include one or more elastic strands or elastic leg bands 32 joined to the leg band portion 33. The leg band 32 may be coextensive with the leg band portion 33, but need not necessarily be so. The leg band 32 may include an elastic material layer (e.g., strands, film, or nonwoven) laminated with one or more layers of extensible nonwoven and/or films. The leg band 32 may be a live stretch or zero-strain stretch laminates. In a live stretch laminate, the elastic material is typically stretched to some extent prior to lamination to an extensible nonwoven. One advantage of live stretch localized stress to the laminate may be reduced during activation. However, live-stretch laminates may require more nonwoven material than zero-strain laminates, and thus be more expensive. The leg band may be attached flush with, laterally inboard, or laterally outboard of the side edge of the outer cover in the crotch region. The leg band 32 and/or leg band portion 33 of the outer cover 22 may be activated continuously or intermittently to provide a stretchable leg opening when the disposable absorbent article is in a fastened configuration.

The disposable absorbent article 20 may include a front waist region 36, a rear waist region 38 opposed to the front waist region 36, and a crotch region 37 located between the front waist region 36 and the rear waist region 38. The waist regions 36 and 38 generally comprise those portions of the disposable absorbent article 20 which, when worn, encircle the waist of the wearer. The crotch region 37 is that portion of the disposable absorbent article 20 which, when the disposable absorbent article 20 is worn, is generally positioned between the legs of the wearer. The waist regions 36 and 38 and the crotch region 37, except for those portions of the article 20 or outer cover 22 that include the leg band portion(s) 33, may collectively be referred to as the body 30 of the article 20 or outer cover 22. As shown in FIG. 9, the outer periphery of the disposable absorbent article 20 is defined by longitudinal side edges 54 and end edges 56. The disposable absorbent article 20 may include longitudinal side edges 54 that are oriented generally parallel to the longitudinal centerline 10. The outer cover 22 may include edges that are coterminous with the longitudinal side edges 54 and/or end edges 56 of the disposable absorbent article 20. Alternatively, the outer cover 22 may have one or more edges that are positioned inboard of the respective edges 54, 56 of the disposable absorbent article 20, but which are oriented in generally the same direction (i.e., parallel to the longitudinal and lateral centerlines 10 and 86).

Disposable absorbent articles such as disposable diapers are generally designed to provide a suitable fit around the waist and legs of a wearer. Due to a variety of physical differences in wearers, the circumferences, shapes, and other physical characteristics of a wearer's waist or legs may vary widely between wearers, and thus require a range of sizes of absorbent articles. Therefore, it may be desirable to provide a disposable absorbent article that is able to adjust to a variety of wearer sizes, for example, by providing an outer cover that has multidirectional elasticity. Such an outer cover may include an outer extensible nonwoven layer that has a cloth-like appearance and feel and an inner elastic layer. The outer and inner layers may be joined to together to form a laminate. In order to provide a disposable diaper or pant with underwear-like properties, it may be desirable to activate all or a portion of the outer cover of such articles in the CD so that when the outer cover is incorporated into the article (e.g., a disposable diaper or training pant), the article will provide a desirable fit by elastically conforming to a wearers body in the waist regions (e.g., across the upper portion of the buttocks). It may also be desirable to activate the leg band portion of the outer cover in the MD to provide 360 degree stretch around the leg opening when the diaper or pant is worn by an intended wearer. In certain embodiments, the leg band portion may be activated in a curvilinear direction to follow the contour of the longitudinal side edge of the outer cover. The different directions of activation (e.g., the CD activated body portion of the outer cover and the MD activated leg band portion of the outer cover) may be spatially separated on the outer cover by one or more buffer zones. The buffer zone may be partially or entirely bounded by and/or contiguous with two or more regions of the disposable absorbent article having different directions of activation. The buffer zone may be between 2 and 30 mm wide. The apparatus and process described herein may be suitable for simultaneously activating such an outer cover without causing undesirable damage to the outer cover web or undesirable stretch lock-up. All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for simultaneously activating a stretchable material in multiple directions, the method comprising:
    feeding the stretchable material into a nip formed between a first rotatable roll and a second rotatable roll, wherein the first and second rolls comprise
        a first region comprising a least one three-dimensional surface feature, the three-dimensional surface feature(s) of the first region of the first roll and the three-dimensional surface feature(s) of the first region of the second roll being complementary to one another and positioned relative to one another such that when the first roll and the second roll are rotated the three-dimensional surface features of the first regions of the first and second rolls intermesh, the intermeshing surface features being operatively configured to activate the stretchable material in a first direction;
        a second region comprising at least one three-dimensional surface feature, the three-dimensional surface feature(s) of the second region of the first roll and the three-dimensional surface feature(s) of the second region of the second roll being complementary to one another and positioned relative to one another such that when the first roll and the second roll are rotated the three-dimensional surface features of the second regions of the first and second rolls intermesh, the intermeshing surface features of the second regions of the first and second rolls being operatively configured to activate the stretchable material in a second direction which is different from the first direction; and
        a circumferential buffer region disposed between the portions of the first and second regions that include three-dimensional surface features.

2. The method of claim 1, wherein the buffer region has a width of between about 2 and 30 mm.

3. The method of claim 1, wherein the buffer region has a width of between about 5 and 20 mm.

4. The method of claim 1, wherein the three-dimensional features of at least one of the first and second regions comprise raised portions having a pitch of at least 1 mm.

5. The method of claim 1, wherein the first and second rolls are configured to rotate 360 degrees, and the first and second rolls are configured to activate the stretchable material two or more times for each 360 degrees of rotation.

6. The method of claim 1, wherein the first and second rolls are configured to rotate 360 degrees and the stretchable material comprises discrete articles, and wherein the first and second rolls are configured to activate two or more articles for each 360 degrees of rotation.

7. The method of claim 1, wherein the rolls are configured to activate the stretchable material intermittently in at least one of the machine direction and the cross direction.

8. The method of claim 1, wherein the first direction is the machine direction and the rolls are configured to continuously activate the stretchable material in the cross direction.

9. The method of claim 1, wherein the first and second directions of activation are selected from the group consisting of a machine direction, a cross direction, a diagonal direction, and a curvilinear direction.

10. The method of claim 1, wherein the stretchable material comprises an extensible material joined to an elastic material, the stretchable material being suitable for use as an outer cover for a disposable absorbent article.

11. The method of claim 10, wherein the stretchable material comprises a body portion and a leg band portion and the first regions are configured to activate the body portion and the second regions are configured to activate the leg band portion.

12. The method of claim 10, wherein the body portion is activated in the cross direction and the leg band portion is activated in the machine direction.

13. The method of claim 12, wherein the leg band portion includes a leg band attached thereto.

14. The method of claim 1, wherein at least one of the first and second rolls comprise an axial buffer region and a circumferential buffer region.

15. The method of claim 1, further comprising a single step of a multi-step diaper manufacturing process.

16. The method of claim 15, wherein the stretchable material is suitable for use as an outer cover in a disposable diaper and the single step comprises activating the outer cover.

17. The method of claim 1, wherein the first and second rolls include a third region configured to provide a third direction of activation that it is different than the first and second directions of activation and wherein a second buffer region is disposed between the third region and at least one of the first and second regions.

18. The method of claim 1, wherein first and second rolls include a third region configured to activate the stretchable material in the second direction, the second and third regions configured to activate different portions of the stretchable material.

19. The method of claim 18, wherein at least a portion of the first and second regions and at least a portion of the first and third regions are separated by a buffer region.

20. The method of claim 18, wherein the second and third regions are respectively disposed on first and second axially opposed ends of the first and second rolls, the second and third regions extending axially inward from their respective ends no more than 60 mm.

* * * * *